United States Patent
Bluemli et al.

(10) Patent No.: US 6,190,169 B1
(45) Date of Patent: Feb. 20, 2001

(54) ANCHORAGE FOR DENTAL PROSTHETICS

(75) Inventors: Markus Bluemli, Biel; Alexis Buchholz, Hauterive; Heiner Kaufmann, Gümligen, all of (CH)

(73) Assignee: Cendres et Métaux SA (CH)

( * ) Notice: Under 35 U.S.C. 154(b), the term of this patent shall be extended for 0 days.

(21) Appl. No.: 09/458,349

(22) Filed: Dec. 10, 1999

(30) Foreign Application Priority Data

Jan. 22, 1999 (EP) .................................................. 98810053

(51) Int. Cl.⁷ .................................................. A61C 13/225
(52) U.S. Cl. .................................................. 433/172
(58) Field of Search .................................. 433/172, 169, 433/177, 178

(56) References Cited

U.S. PATENT DOCUMENTS

| | | | |
|---|---|---|---|
| 3,991,472 | * 11/1976 | Lukesch | 433/169 |
| 4,547,156 | * 10/1985 | Hader | 433/172 |
| 4,573,923 | 3/1986 | Poveromo | 433/181 |
| 5,417,570 | * 5/1995 | Zuest et al. | 433/177 |

FOREIGN PATENT DOCUMENTS

| | | |
|---|---|---|
| 380292 | 9/1964 | (CH) . |
| 633440 | 12/1982 | (CH) . |

* cited by examiner

*Primary Examiner*—John J. Wilson
*Assistant Examiner*—Melba Bumgarner
(74) *Attorney, Agent, or Firm*—Ostrolenk, Faber, Gerb & Soffen, LLP

(57) ABSTRACT

The anchorage for dental prosthetics includes a male member which is attachable to a tooth and comprises, in a preferred embodiment, a ball head, and a female member which is attachable to a dental prosthesis. The female member comprises an internal thread and a lamellar insert having a threaded portion for receiving and retaining the ball head, the retention force of the lamellar insert being continuously adjustable by rotation thereof. A female member of this kind with a screwed lamellar insert allows a fine adjustment of the retention of the male member in accordance with the actual conditions.

12 Claims, 1 Drawing Sheet

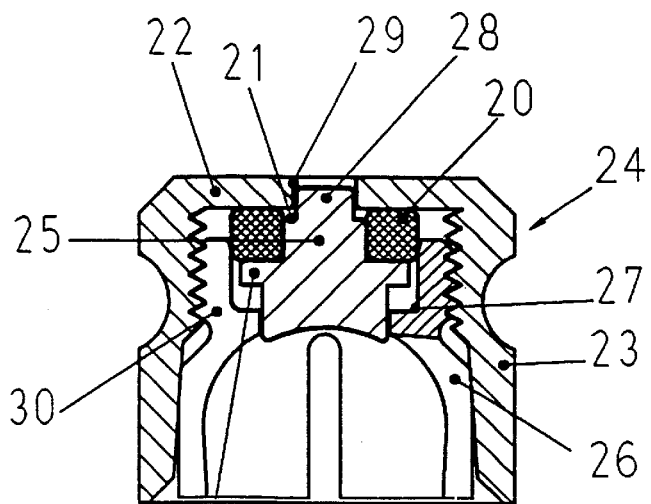
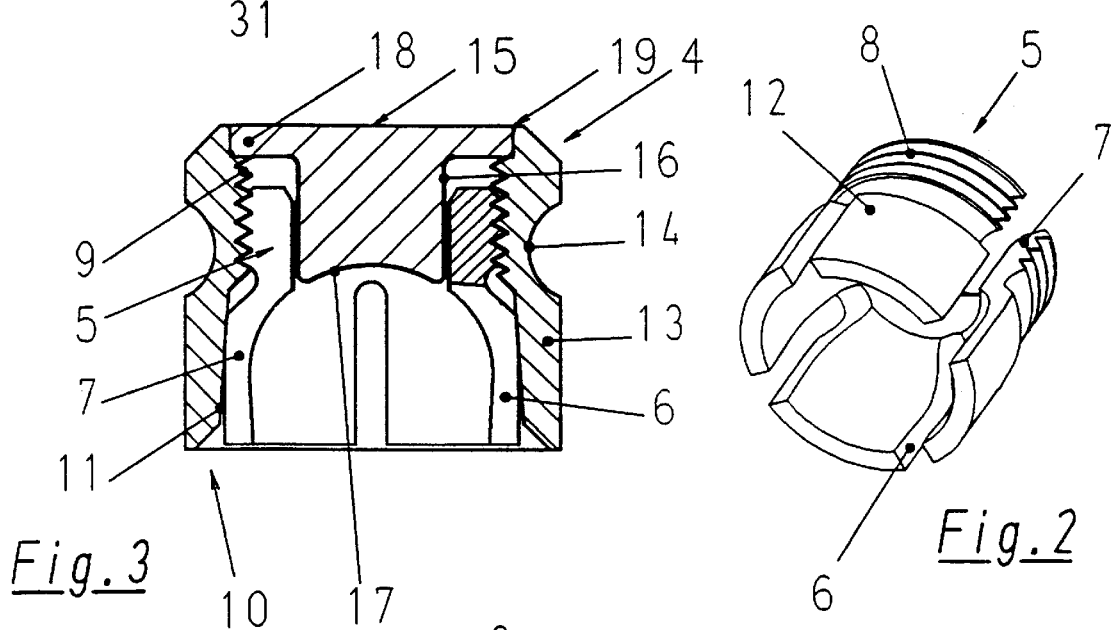
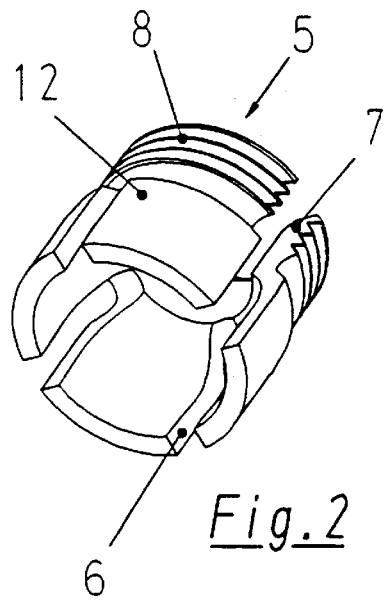
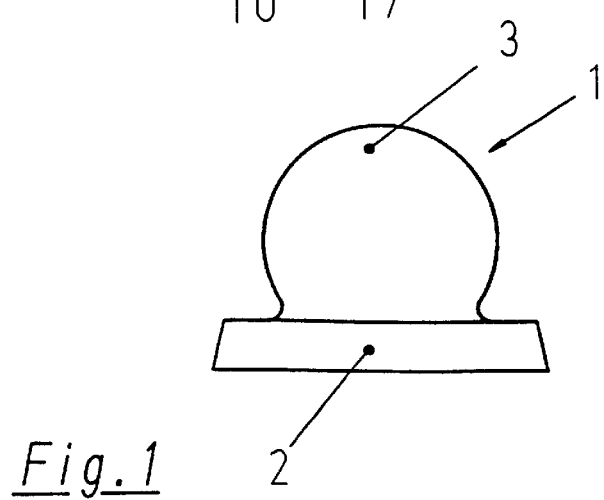

ANCHORAGE FOR DENTAL PROSTHETICS

BACKGROUND OF THE INVENTION

The present invention refers to an anchorage for dental prosthetics, comprising a male member which is attachable to a tooth and provided with a head, and a female member which is attachable to a dental prosthesis. An anchorage of this kind having a ball head is being marketed by the applicant in the form of a resilient anchorage according to Dr. Dalla Bona under the commercial name DALBO. In the case of resilient anchorages comprising ball heads, it is relatively difficult to adjust the retention force, and different solutions have been suggested, e.g. the use of spring-loaded balls, amongst others. In one of the commercial embodiments, the female member is provided with lamellas.

SUMMARY OF THE INVENTION

On the background of this prior art, it is the object of the present invention to improve a resilient anchorage comprising a head in such a manner that an easily and safely adjustable retention is obtained. This object is attained by an anchorage wherein the female member comprises an internal thread and a lamellar insert receiving and retaining the head of the male member, the retention force of the lamellar insert being continuously adjustable by rotation thereof. Further developments of the invention are defined in the dependent claims.

BRIEF DESCRIPTION OF THE DRAWINGS

The invention is explained in more detail hereinafter with reference to exemplary embodiments.

FIG. 1 shows male member having a ball head;

FIG. 2 shows a perspective view of a lamellar insert according to the invention;

FIG. 3 shows a cross-sectional view of a first embodiment of a female member of the invention; and FIG. 4 shows a cross-sectional view of a second embodiment of a female member of the invention.

DETAILED DESCRIPTION OF THE INVENTION

FIG. 1 shows a male member 1 comprising a base 2 for its attachment to a root cap, e.g. by casting, soldering, welding or cementing, as well as a ball head 3. Basically, the male member may be manufactured from any suitable dental alloy or, if it is used for molding purposes, from plastic materials, but it is preferably made of a palladium- and copper-free alloy allowing an attachment by casting, or from pure titanium. Furthermore, the head need not be a ball head, any other form like a cylindrical or other wise shaped head is possible.

FIG. 2 illustrates a lamellar insert 5 which is adapted to be screwed into a female member 4 and which in the present embodiment comprises three non-continuous slits 6 and one continuous slit 7, thus resulting in four lamellas. The continuous slit serves for the contraction of the entire lamellar insert while the slits serve for its compression. The lamellar insert further comprises a threaded portion 8, and it is manufactured from one of the metals or metal alloys indicated above.

Female member 4 or 24 illustrated in FIGS. 3 or 4 comprises an internal thread 9 which corresponds to threaded portion 8 and allows to turn in resp. screw in the lamellar insert. Between the inner end of the thread and the free end 10 of the female member, the inner surface 11 of the female member is conical with respect to its external surface while the internal diameter diminishes towards the inner thread. Thus, the lamellas of retention portion 12 of lamellar insert 5 are bent inwards when it is screwed into the female member, thus allowing a continuous adjustment, i.e. in this case an increase, of the retention force acting upon the ball head.

Female member 4 illustrated in FIG. 3 comprises a housing 13 in the form of a closed cap essentially, the housing of the female member being manufactured from the above-mentioned metals or metal alloys. The housing further comprises a circular retention groove 14 on the outside which serves to assist the anchorage of the housing after its attachment to the prosthesis by polymerization or cementing. The housing may further comprise notches or grooves for rotational securing.

The housing further comprises a stop element 15 having a cylindrical body 16 with a spherical surface 17 which serves as a stop for the ball head of the male member and thus ensures a precise and constant position of the ball head in the female member. It is understood that the stop surface is adapted to the form of the head and need not be spherical as in this example. In the embodiment of FIG. 3, the stop element is provided with a front plate 18 which is inserted resp. pressed into the end opposite the free end 19 of the housing and forms the end wall of the housing. Stop element 15 is manufactured from the same materials as the housing of the female member, the lamellar insert, or the male member.

The stop element ensures that the male member is always inserted in the female member in exactly the same position, while the lamellar insert allows a continuous and precise adjustment of the retention force and a precise adaptation to different conditions.

FIG. 4 illustrates and alternative embodiment which allows to attenuate the forces acting between the female and the male member. This attenuation is obtained by means of a damping member 20 such as an O-ring adapted to such purposes. As opposed to the stop element 15 of FIG. 3, the cylindrical body of stop element 21 comprises a stepped portion 31 and a cylindrical portion 25 of a smaller diameter around which damping member 20 is disposed. Consequently, the damping member is disposed between the stepped portion of the stop element and the end wall 22 of housing 23 of female member 24.

The threaded portion 30 of lamellar insert 26 comprises a recess 27 in order to make room for damping member 20. Otherwise, the design of the lamellar insert is the same as in the preceding embodiment. At the end opposite its spherical surface 17, stop element 21 is provided with a peg which is adjusted to a bore 29 in end wall 22 in a sliding manner. The inner part of stop element 21 with spherical surface 17 is the same as in the preceding example.

It is apparent from the description and from FIG. 4 that damping element 20 both serves as a stop in the insertion of the male member and as a damping member or buffer of chewing movements, and additionally serves a third function as a sealing element which prevents that impurities may enter the prosthesis.

What is claimed is:

1. Anchorage for dental prosthetics, comprising a male member which is attachable to a tooth and provided with a head, and a female member which is attachable to a dental prosthesis, wherein said female member comprises an internal thread and a lamellar insert receiving and retaining said head of said male member, the retention force of said lamellar insert being continuously adjustable by rotation thereof.

2. The anchorage of claim 1, wherein the inner surface of said female member which contacts the retention portion of said lamellar insert is conically tapered from its free end to the inside.

3. The anchorage of claim 1, wherein said female member comprises a stop element which is disposed inside said lamellar insert and comprises a surface serving as a stop for said head.

4. The anchorage of claim 3, wherein said stop element comprises a front plate which is inserted at the end opposite the free end of the housing and forms the end wall of the latter.

5. The anchorage of claim 3, wherein said stop element is slidable in the housing of the female member, and a damping member is disposed between said stop element and the housing of the female member.

6. The anchorage of claim 5, wherein said stop element comprises a cylindrical body having a stepped portion and a peg sliding in a bore in the end wall of the housing, said damping member being disposed between said stepped portion and said end wall.

7. The anchorage of claim 3, wherein and said stop surface for the head of the male member is spherical.

8. The anchorage of claim 3, wherein and said stop surface has a form which is adapted to the form of the head of the male member.

9. The anchorage of claim 1, wherein said lamellar insert comprises three slits extending up to said threaded portion and one continuous slit.

10. The anchorage of claim 1, wherein said male member and said female member and their parts are manufactured from a dental alloy or from pure titanium.

11. The anchorage of claim 1, wherein said head of the male member is a ball head.

12. The anchorage of claim 1, wherein said head for the male member is cylindrical.

* * * * *